United States Patent
Adams

(10) Patent No.: US 11,759,332 B2
(45) Date of Patent: Sep. 19, 2023

(54) JOINT OR SEGMENTAL BONE IMPLANT FOR DEFORMITY CORRECTION

(71) Applicant: Stryker European Operations Limited, Carrigtwohill (IE)

(72) Inventor: Samuel Adams, Raleigh, NC (US)

(73) Assignee: Stryker European Operations Limited

( * ) Notice: Subject to any disclaimer, the term of this patent is extended or adjusted under 35 U.S.C. 154(b) by 659 days.

(21) Appl. No.: 16/729,739

(22) Filed: Dec. 30, 2019

(65) Prior Publication Data

US 2020/0129303 A1 Apr. 30, 2020

Related U.S. Application Data

(60) Division of application No. 15/447,227, filed on Mar. 2, 2017, now Pat. No. 10,517,737, which is a
(Continued)

(51) Int. Cl.
*A61F 2/46* (2006.01)
*A61F 2/42* (2006.01)
(Continued)

(52) U.S. Cl.
CPC ............ *A61F 2/4606* (2013.01); *A61B 17/72* (2013.01); *A61B 17/7291* (2013.01);
(Continued)

(58) Field of Classification Search
CPC .. A61B 17/7291; A61F 2/4202; A61F 2/4606; A61F 2002/30242; A61F 2002/30243
See application file for complete search history.

(56) References Cited

U.S. PATENT DOCUMENTS

| 4,820,305 A | 4/1989 | Harms et al. |
| 4,936,848 A | 6/1990 | Bagby |

(Continued)

FOREIGN PATENT DOCUMENTS

| AU | 2016267051 A1 | 12/2017 |
| CA | 2986752 A1 | 12/2016 |

(Continued)

OTHER PUBLICATIONS

Rasmussen et al., "Implantable Medical Devices With Friction Enhancing Needle Protrusions, and Methods for Making Same Using Additive Manufacturing Techniques", U.S. Appl. No. 13/530,048, filed Jun. 21, 2012.
(Continued)

*Primary Examiner* — William H Matthews
(74) *Attorney, Agent, or Firm* — Lerner David LLP

(57) ABSTRACT

An implant is provided for use in an ankle joint between reconditioned end surfaces established on a distal end of an upper tibia bone and an opposing lower talus bone. The implant comprises a substantially porous rigid component adapted to be anchored against the upper tibia reconditioned end surface and the lower talus reconditioned end surface. The component defining an opening therethrough. An intramedullary nail is configured to pass through the opening in the component when the nail is driven through the talus and into the tibia.

20 Claims, 10 Drawing Sheets

Related U.S. Application Data continuation of application No. 15/162,525, filed on May 23, 2016, now Pat. No. 10,045,854.

(60) Provisional application No. 62/165,376, filed on May 22, 2015.

(51) Int. Cl.
  *A61B 17/72* (2006.01)
  *A61B 17/68* (2006.01)
  *A61F 2/30* (2006.01)
  *A61B 17/56* (2006.01)
  *A61F 2/00* (2006.01)

(52) U.S. Cl.
  CPC ............ *A61F 2/4202* (2013.01); *A61B 17/68* (2013.01); *A61B 2017/564* (2013.01); *A61F 2/0077* (2013.01); *A61F 2002/3028* (2013.01); *A61F 2002/30242* (2013.01); *A61F 2002/30517* (2013.01); *A61F 2002/30593* (2013.01); *A61F 2002/30604* (2013.01); *A61F 2002/4205* (2013.01); *A61F 2002/4207* (2013.01); *A61F 2002/4212* (2013.01); *A61F 2002/4217* (2013.01); *A61F 2250/0024* (2013.01)

(56) References Cited

U.S. PATENT DOCUMENTS

| | | |
|---|---|---|
| 5,281,226 A | 1/1994 | Davydov et al. |
| 5,609,367 A | 3/1997 | Eusebi et al. |
| 5,702,451 A | 12/1997 | Biedemnann et al. |
| 6,086,613 A | 7/2000 | Camino et al. |
| 6,193,755 B1 | 2/2001 | Metz-Stavenhagen et al. |
| 6,193,756 B1 | 2/2001 | Studer et al. |
| 6,200,348 B1 | 3/2001 | Biedemnann et al. |
| 6,206,924 B1 | 3/2001 | Timm |
| 6,579,293 B1 | 6/2003 | Chandran |
| 6,585,770 B1 | 7/2003 | White et al. |
| 6,663,669 B1 | 12/2003 | Reiley |
| 6,673,116 B2 | 1/2004 | Reiley |
| 6,706,924 B2 | 3/2004 | Schelhaas et al. |
| 6,902,581 B2 | 6/2005 | Walkenhorst et al. |
| 6,931,812 B1 | 8/2005 | Lipscomb |
| 7,087,200 B2 | 8/2006 | Taboas et al. |
| 7,244,273 B2 | 7/2007 | Pedersen et al. |
| 7,314,488 B2 | 1/2008 | Reiley |
| 7,641,697 B2 | 1/2010 | Reiley |
| 7,717,920 B2 | 5/2010 | Reiley |
| 7,855,062 B2 | 12/2010 | Harlow et al. |
| 8,062,365 B2 | 11/2011 | Schwab |
| 8,114,647 B2 | 2/2012 | Harlow et al. |
| 8,278,094 B2 | 10/2012 | Harlow et al. |
| 8,292,967 B2 | 10/2012 | Brown et al. |
| 8,354,258 B2 | 1/2013 | Jung et al. |
| 8,367,384 B2 | 2/2013 | Harlow et al. |
| 8,430,930 B2 | 4/2013 | Hunt |
| 8,430,950 B2 | 4/2013 | Kuske et al. |
| 8,485,820 B1 | 7/2013 | Mi |
| 8,492,143 B2 | 7/2013 | Harlow et al. |
| RE44,501 E | 9/2013 | Janna et al. |
| 8,532,806 B1 | 9/2013 | Masson |
| 8,545,572 B2 | 10/2013 | Olson |
| 8,682,619 B2 | 3/2014 | Amodei et al. |
| 8,709,089 B2 | 4/2014 | Lang et al. |
| 8,734,823 B2 | 5/2014 | Amodei et al. |
| 8,808,303 B2 | 8/2014 | Stemniski et al. |
| 8,808,389 B2 | 8/2014 | Reiley |
| 8,900,865 B2 | 12/2014 | Harlow et al. |
| 8,906,022 B2 | 12/2014 | Krinke et al. |
| 8,975,074 B2 | 3/2015 | Harlow et al. |
| 8,999,711 B2 | 4/2015 | Harlow et al. |
| 9,005,943 B2 | 4/2015 | Harlow et al. |
| 9,005,944 B2 | 4/2015 | Harlow et al. |
| 9,020,788 B2 | 4/2015 | Lang et al. |
| 9,023,630 B2 | 5/2015 | Harlow et al. |
| 9,061,075 B2 | 6/2015 | Harlow et al. |
| 9,066,764 B2 | 6/2015 | Perez |
| 9,271,845 B2 | 3/2016 | Hunt et al. |
| 9,364,330 B2 | 6/2016 | Lindsey et al. |
| 9,364,896 B2 | 6/2016 | Christensen et al. |
| 9,421,108 B2 | 8/2016 | Hunt |
| 9,456,901 B2 | 10/2016 | Jones et al. |
| 9,545,317 B2 | 1/2017 | Hunt |
| 9,549,823 B2 | 1/2017 | Hunt et al. |
| 9,572,669 B2 | 2/2017 | Hunt et al. |
| 9,636,226 B2 | 5/2017 | Hunt |
| 9,636,276 B2 | 5/2017 | Woolston |
| 9,642,632 B2 | 5/2017 | Stemniski et al. |
| 9,724,203 B2 | 8/2017 | Nebosky et al. |
| 9,757,235 B2 | 9/2017 | Hunt et al. |
| 9,814,595 B2 | 11/2017 | Biedemnann et al. |
| 9,890,827 B2 | 2/2018 | Schaedler et al. |
| 9,987,137 B2 | 6/2018 | Hunt et al. |
| 9,993,277 B2 | 6/2018 | Krinke et al. |
| 9,999,516 B2 | 6/2018 | Hunt |
| 10,039,557 B2 | 8/2018 | Stemniski et al. |
| 10,045,854 B2 | 8/2018 | Adams |
| 10,064,726 B1 | 9/2018 | Wei |
| 10,070,962 B1 | 9/2018 | Moore et al. |
| 10,098,746 B1 | 10/2018 | Moore et al. |
| 10,130,485 B2 | 11/2018 | Biedemnann et al. |
| 10,166,033 B2 | 1/2019 | Reiley et al. |
| 10,182,832 B1 | 1/2019 | Saltzman et al. |
| 10,213,309 B2 | 2/2019 | Lindsey et al. |
| 2005/0015154 A1 | 1/2005 | Lindsey et al. |
| 2006/0147332 A1 | 7/2006 | Jones et al. |
| 2010/0174377 A1 | 7/2010 | Heuer |
| 2011/0125284 A1 | 5/2011 | Gabbrielli et al. |
| 2011/0172826 A1 | 7/2011 | Amodei et al. |
| 2011/0200478 A1 | 8/2011 | Billiet et al. |
| 2011/0313532 A1 | 12/2011 | Hunt |
| 2013/0030529 A1 | 1/2013 | Hunt |
| 2013/0090739 A1 | 4/2013 | Linares et al. |
| 2013/0101637 A1 | 4/2013 | Harlow et al. |
| 2013/0123935 A1 | 5/2013 | Hunt et al. |
| 2013/0158672 A1 | 6/2013 | Hunt |
| 2013/0218278 A1 | 8/2013 | Wolfe et al. |
| 2014/0121776 A1 | 5/2014 | Hunt |
| 2014/0277575 A1 | 9/2014 | Landgrebe et al. |
| 2014/0277576 A1 | 9/2014 | Landgrebe et al. |
| 2014/0288649 A1* | 9/2014 | Hunt ...................... A61F 2/447 623/16.11 |
| 2014/0288650 A1 | 9/2014 | Hunt |
| 2015/0064146 A1 | 3/2015 | Harlow et al. |
| 2015/0258735 A1 | 9/2015 | O'Neill et al. |
| 2015/0282946 A1 | 10/2015 | Hunt |
| 2016/0089245 A1 | 3/2016 | Early et al. |
| 2016/0287388 A1 | 10/2016 | Hunt et al. |
| 2016/0338842 A1 | 11/2016 | Adams |
| 2017/0172752 A1 | 6/2017 | Adams |
| 2017/0216035 A1 | 8/2017 | Hunt |
| 2017/0319344 A1 | 11/2017 | Hunt |
| 2017/0319349 A1 | 11/2017 | Kowalczyk |
| 2017/0360488 A1 | 12/2017 | Kowalczyk et al. |
| 2018/0028242 A1 | 2/2018 | Parekh et al. |
| 2018/0064540 A1 | 3/2018 | Hunt et al. |
| 2018/0085230 A1 | 3/2018 | Hunt |
| 2018/0199972 A1 | 7/2018 | Krinke et al. |
| 2018/0360611 A1 | 12/2018 | Adams |
| 2019/0060077 A1 | 2/2019 | Hunt et al. |

FOREIGN PATENT DOCUMENTS

| | | |
|---|---|---|
| CN | 201164511 Y | 12/2008 |
| CN | 201200499 Y | 3/2009 |
| CN | 107835669 A | 3/2018 |
| EP | 1800627 A2 | 6/2007 |
| EP | 3297553 A1 | 3/2018 |
| FR | 373990 A | 5/1907 |
| GB | 190118231 A | 11/1901 |
| GB | 595628 A | 12/1947 |
| GB | 972282 A | 10/1964 |

(56) References Cited

FOREIGN PATENT DOCUMENTS

| | | | |
|---|---|---|---|
| JP | 201851913 | A | 4/2018 |
| WO | 9933641 | A1 | 7/1999 |
| WO | 2004110309 | A2 | 12/2004 |
| WO | 2005051233 | A2 | 6/2005 |
| WO | 2008022206 | A2 | 2/2008 |
| WO | 2011082905 | A1 | 7/2011 |
| WO | 20110123110 | A1 | 10/2011 |
| WO | 2013006778 | A2 | 1/2013 |
| WO | 20130119907 | A1 | 8/2013 |
| WO | 2016191393 | A1 | 12/2016 |

OTHER PUBLICATIONS

International Search Report from PCT/US2016/033835, dated Aug. 26, 2016, pp. 1-4.
Thimmesch, D., 3D Printed Bone Implant Saves a Virginia Woman's Injured Leg, 3D Printing/Health 3D Printing, Dec. 10, 2014, WRAL.com.

* cited by examiner

JOINT OR SEGMENTAL BONE IMPLANT FOR DEFORMITY CORRECTION

CROSS-REFERENCE TO RELATED APPLICATIONS

This application is divisional of U.S. patent application Ser. No. 15/447,227, filed Mar. 2, 2017, which is a continuation application of U.S. patent application Ser. No. 15/162,525, filed May 23, 2016, which is related to U.S. provisional application No. 62/165,376, filed May 22, 2015, entitled "JOINT OR SEGMENTAL BONE IMPLANT FOR DEFORMITY CORRECTION", naming Samuel Adams as the inventor, the contents of each of which are incorporated herein by reference.

BACKGROUND OF THE INVENTION

A medical implant is described and, more particularly, a medical implant for use in joint or segmental bone defects for deformity correction with or without obtaining arthrodesis.

Implants may be used in humans or animals to support or secure one or more bones. Once implanted, the implant may provide support between the bones and bone growth may take place around and through the implant to at least partially fuse the bones for long-term support.

There is a need for an improved medical implant for use in body areas, such as bones of the foot and ankle.

BRIEF SUMMARY OF THE INVENTION

An implant is provided for use in an ankle joint between reconditioned end surfaces established on a distal end of an upper tibia bone and an opposing lower talus bone. The implant comprises a substantially porous rigid component adapted to be anchored against the upper tibia reconditioned end surface and the lower talus reconditioned end surface. The component defining an opening therethrough. An intramedullary nail is configured to pass through the opening in the component when the nail is driven through the talus and into the tibia.

A method of securing an ankle joint is also provided. The method comprises the steps of reconditioning end surfaces on a distal end of an upper tibia bone and an opposing lower talus bone of the ankle joint. A substantially porous rigid component is positioned against the upper tibia reconditioned end surface and the lower talus reconditioned end surface. The component defining an opening therethrough. An intramedullary nail configured to be driven through the through the talus and the opening in the component and into the tibia.

BRIEF DESCRIPTION OF THE DRAWINGS

For a more complete understanding of the bone implant, reference should now be had to the embodiments shown in the accompanying drawings and described below. In the drawings.

DETAILED DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGS. Indeed, the components may be oriented in any direction and the terminology, therefore, should be understood as encompassing such variations unless specified otherwise.

Figure 1:
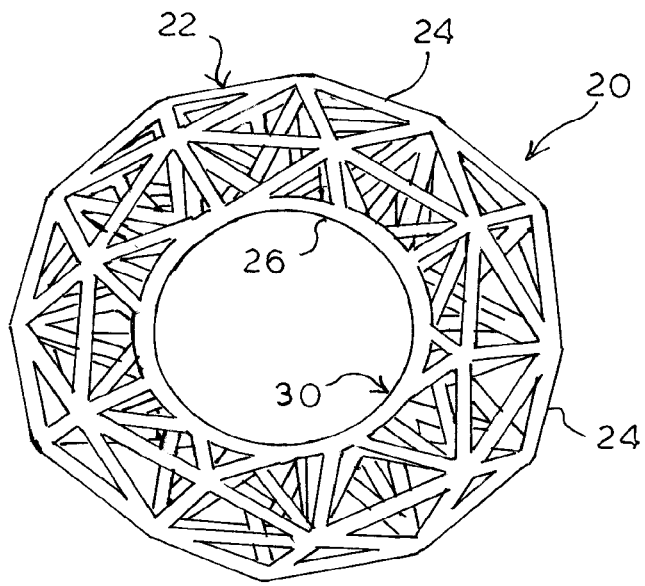
FIG. 1 is a top plan view of an embodiment of a joint or segmental bone implant.
Figure 2:
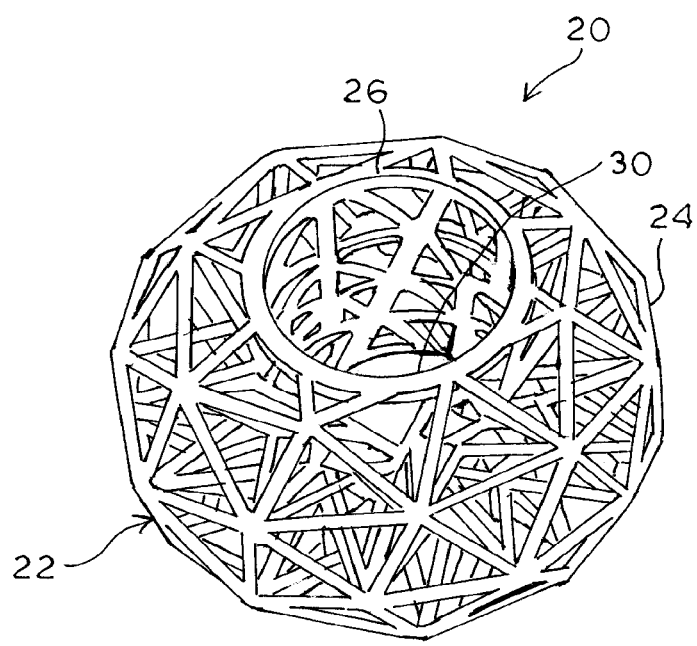
FIG. 2 is a top perspective view of the bone implant as shown in FIG. 1.

Referring now to FIGS. 1 and 2, there is shown an embodiment of a medical joint or segmental bone implant for deformity correction and generally designated at 20. The implant 20 comprises a porous web structure 22 configured to interface with human bone tissue. The web structure 22 extends throughout the implant 20 to provide support. The web structure 22 disperses the stress of compressive forces throughout implant 20, wherein the implant 20 is supported against tensile, compressive, and shear forces. The web structure 22 can be further employed to receive and distribute throughout the implant 20 loading forces of the surrounding tissue. The web structure 22 may also reinforce the implant 20 along multiple planes.

In one embodiment, the web structure 22 is formed with interconnected triangular-shaped building blocks. The result is a web structure 22 formed from a pattern of triangularly-shaped geometrical building blocks. The triangularly-shaped building blocks may form tetrahedrons that may also be used as building blocks. Other patterns from the triangles are also contemplated. Each tetrahedron may include four triangular faces in which three of the four triangles meet at each vertex. At least two of the plurality of tetrahedrons are coupled together via one or more common components connecting two respective vertices on each of the two tetrahedrons such that two tetrahedrons share a common unit to form a hexahedron.

Figure 9:
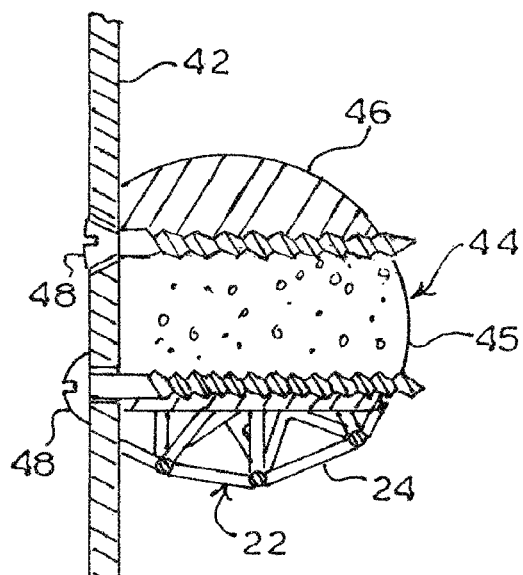
FIG. 9 is an elevation view of a third embodiment of a bone implant having a planar surface to accommodate a plate or other device.
Figure 10:
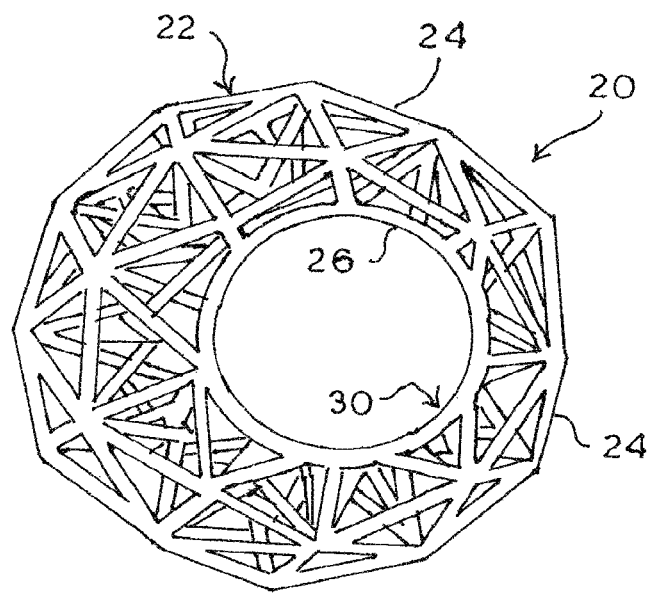
FIG. 10 is an elevation view of a fourth embodiment of a bone implant positioned in a foot and ankle joint.
Figure 14:
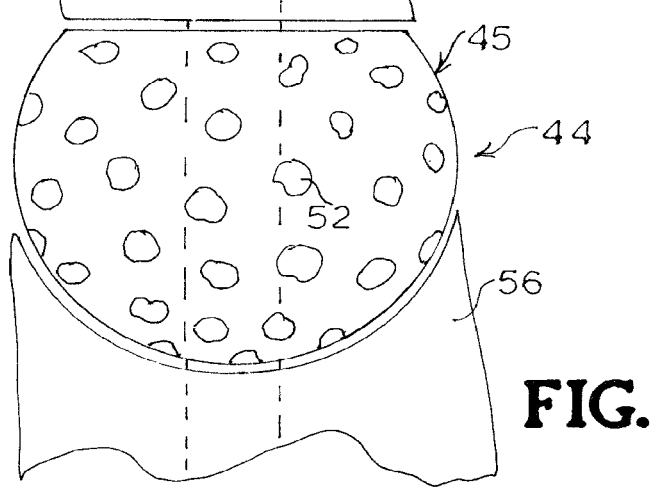
FIG. 14 is schematic elevation view of a seventh embodiment of a bone implant shown between two portions of bone.

In one embodiment, the porous web structure 22 is configured to form a substantially spherical structure as shown in FIGS. 1 and 2. The implant 20 can have a diameter of at least about 38 mm to about 40 mm. However, it is understood that the design of the implant 20 may be sized appropriately to meet specified dimensions of the implantation site. In some embodiments, multiple implants of different sizes may be constructed and delivered in a kit. A medical health professional may choose an implant (e.g., according to a needed size) during surgery. It is understood that while the embodiment of the implant 20 has been described with respect to a particular spherically-shaped web structure, various shapes of web structures are contemplated. For example, a portion of the spherical implant may be removed to form an implant 44 having a planar side (FIG. 9). In another embodiment shown in FIG. 14, the implant 54 may be egg-shaped (FIG. 14).

The implant 20 may be formed from a biocompatible material such as a titanium alloy (e.g., y-titanium aluminides), cobalt, chromium, stainless steel, polyetheretherketone (PEEK), ceramics, or other suitable material. The implant 20 may be made through a rapid prototyping process (e.g., electron beam melting (EBM) process). Other processes are also possible, such as injection molding, casting, sintering, selective laser sintering (SLS), direct metal laser sintering (DMLS), etc). SLS may include laser-sintering of high-performance polymers such as that provided by EOS of North America, Inc., headquartered in Novi, Mich., U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 1 1 provided by EOS of North America, Inc. Multiple parts may be cast or injection molded and joined together (e.g., through welding, melting, etc.). For example, individual components 24 forming the implant 20 may be generated separately (e.g., by casting, injection molding, etc.) and welded together to form the implant 20. The porous web structure 22 may be made according to the disclosure of International Application No. PCT/US2012/045717, filed Jul. 6, 2012, and published Jan. 10, 2013, as International Publication No. WO 2013/006778, the contents of which are hereby incorporated by reference in their entirety.

Figure 12:
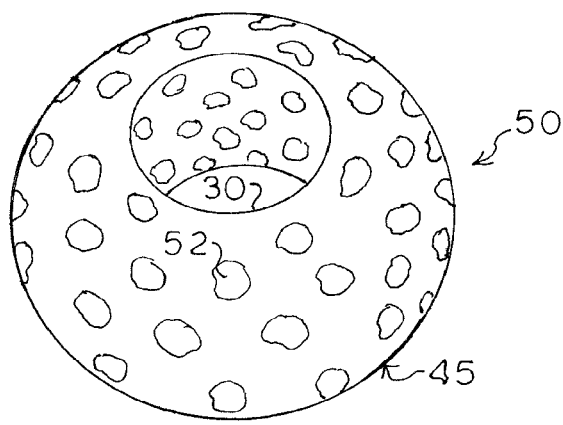
FIG. 12 is a perspective view of a sixth embodiment of a bone implant for use in a foot and ankle joint.

In another embodiment shown in FIG. 12 and generally designated at 50, the web structure 22 of the implant 50 may be formed from a generally porous material having random openings 45.

The implant 20, 50 may include a top face 26 and an opposed bottom face 28 wherein at least a portion of the top face 26 and the bottom face 28 are generally parallel to one another. In use, the top and bottom faces 26, 28 are configured to be disposed in contact, or near contact, of an adjacent bony structure for contacting the bony structure during use to adhere or couple with the adjacent structure when implanted. As depicted, for example, the implant 20, 50 is intended to sandwich between two adjacent bony structures interfacing with bone structure of a foot and ankle joint 34. The top contact face 26 may couple to a portion of the first bony structure disposed above implant 20 and the bottom contact face 28 may couple to the second bony structure disposed below implant 20.

The web structure 22 defines openings configured to define open volume to enable bone growth through the openings of the web structure 22, thereby enhancing coupling of the implant 20 to the adjacent bony structure. At least a portion of the web structure 22 is in contact, or near contact, with the adjacent bony structure, thereby enabling bone growth to extend into or through at least a portion of open volume of the web structure 22 such that the bone growth interlocks with the web structure 22 of the implant 20. The interlocking of the bone growth and the web structure 22 may rigidly fix the implant 20 in a fixed location relative to the bony structure. For example, a web structure 22 may define an open space for bone growth therethrough, thereby enabling bone through growth to interlock the bone structure and the web structure 22 with one another to couple the implant 20 to the bony structure at or near the contact surface. Such interlocking bone through growth may inhibit movement between the implant 20 and the bony structure, which could otherwise lead to loosening, migration, subsidence, or dislodging of the implant 20 from the intended position.

The web structure 22 of the implant 20 may also provide surface area for bone graft fusion. For example, the voids in the web structure 22 of the implant 20 may be filled with, or surfaces of the web structure 22 may be coated with, bone grafting material, a biologic, growth factor or the like. The web structure 22 extending throughout the implant 20 may add additional surface area on the surface of the components 24 to fuse to the bone graft material and prevent the bone graft material from loosening or migrating from the implant 20. In some embodiments, the web structure 22 may also support and facilitate bone in-growth. For example, adjacent bone in an ankle joint may grow over at least a portion of the components 24 of the implant 22. The bone growth and engagement between the bone growth and the implant 20 may further stabilize the implant. In some embodiments, the surfaces of the implant 20 may be formed with a rough surface to assist in bone in-growth adhesion.

At least a portion of the open volume of the web structure 22 of the implant 20 may be filled with bone growth material. For example, cancellous bone may be packed into the openings internally of the implant 20. In some embodiments, at least a portion of the surfaces of implant 20 may be coated or treated with a material intend to promote bone growth or bone adhesion or an antimicrobial agent to prevent infections. For example, in some embodiments, the surface of the web structure 22 may be coated with a biologic or a bone growth factor. For example, the biologic or growth factor may be physically secured to the web structure 22 in a central portion of the implant 20 provided there is the physical attachment of the biologic or growth factor. The biologic may include a coating, such as hydroxyapatite, bone morphaginic protein (BMP), insulin-like growth factors I and II, transforming growth factor-beta, acidic and basic fibroblast growth factor, platelet-derived growth factor, or similar bone growth stimulant that facilitates good biological fixation between the bone growth and a surface of the implant 20. The bone growth factor may include a naturally occurring substance capable of stimulating cellular growth, proliferation and cellular differentiation (e.g., a protein or steroid hormone).

Figure 3:
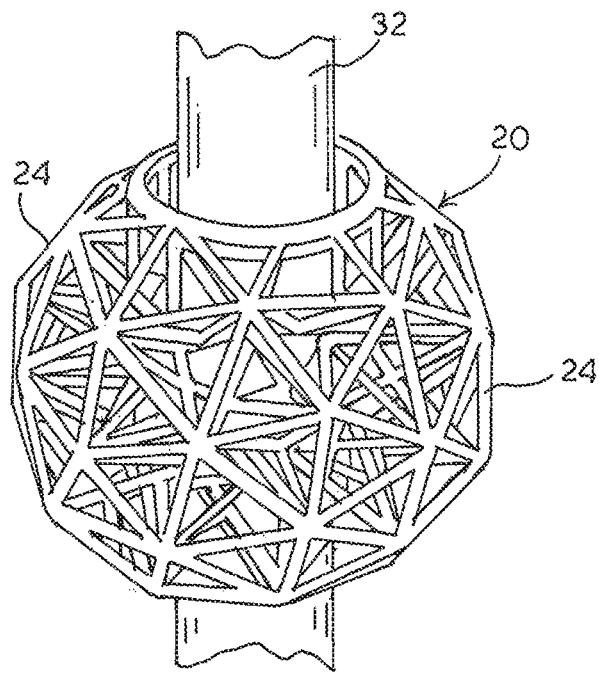
FIG. 3 is a perspective view of the bone implant as shown in FIG. 1 receiving a portion of an intramedullary nail.
Figure 4:
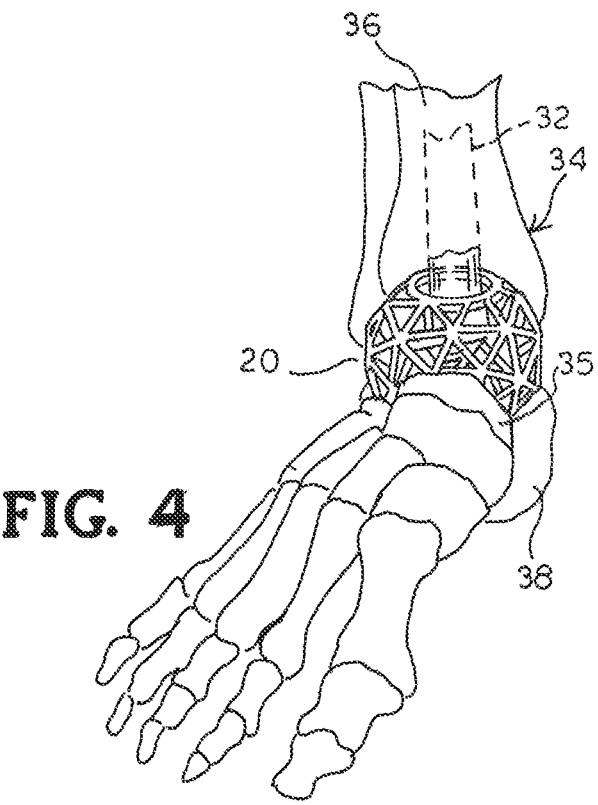
FIG. 4 is a perspective view of the bone implant as shown in FIG. 1 positioned in a foot and ankle joint.
Figure 5:
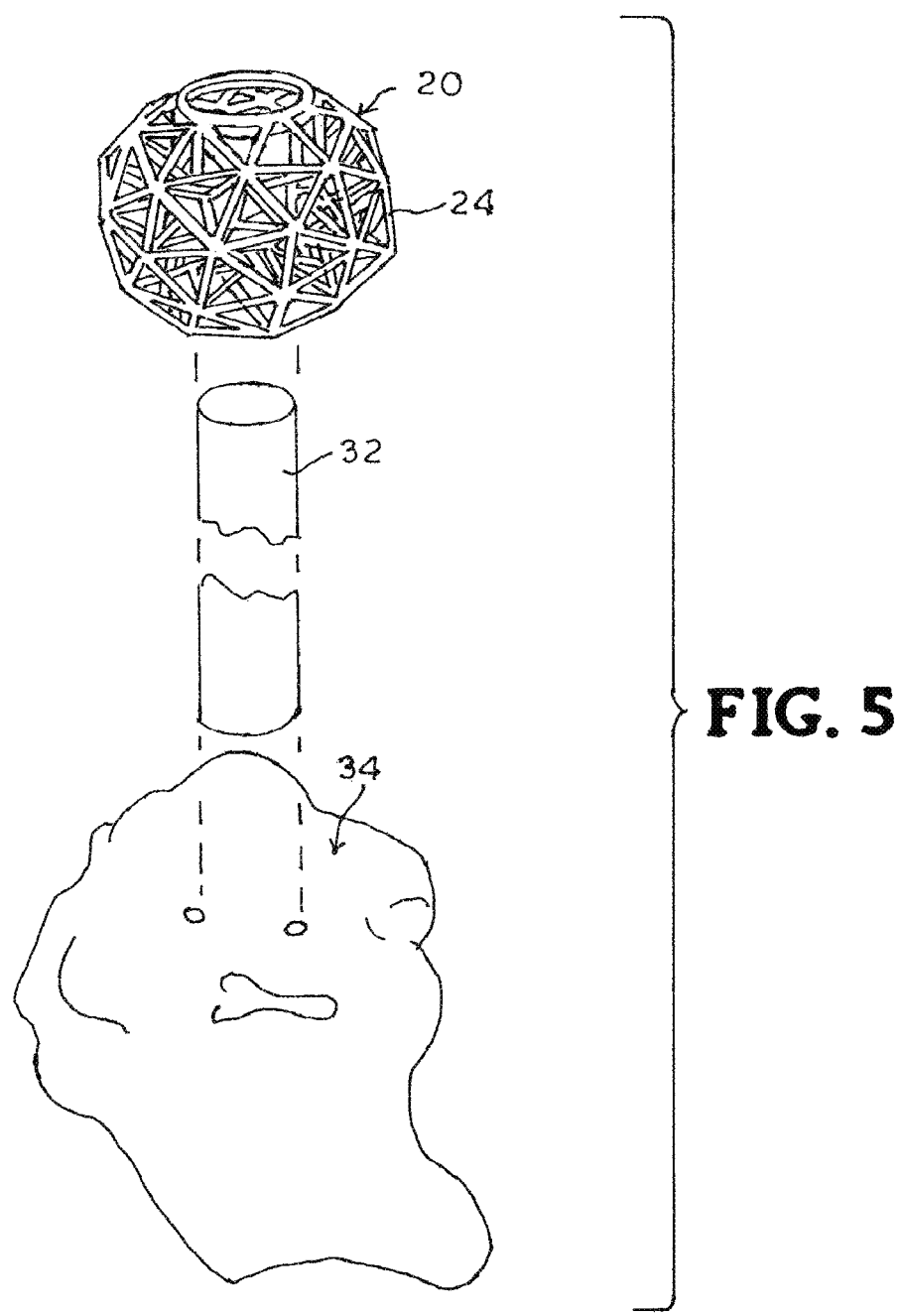
FIG. 5 is an exploded perspective view of the bone implant and the foot and ankle joint as shown in FIG. 4.
Figure 6A:
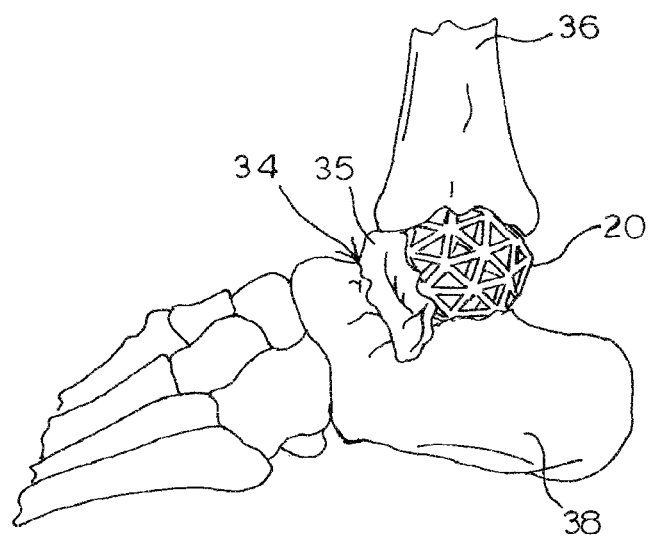
FIG. 6A is a side elevation view of the bone implant as shown in FIG. 1 positioned in a foot and ankle joint.
Figure 6B:
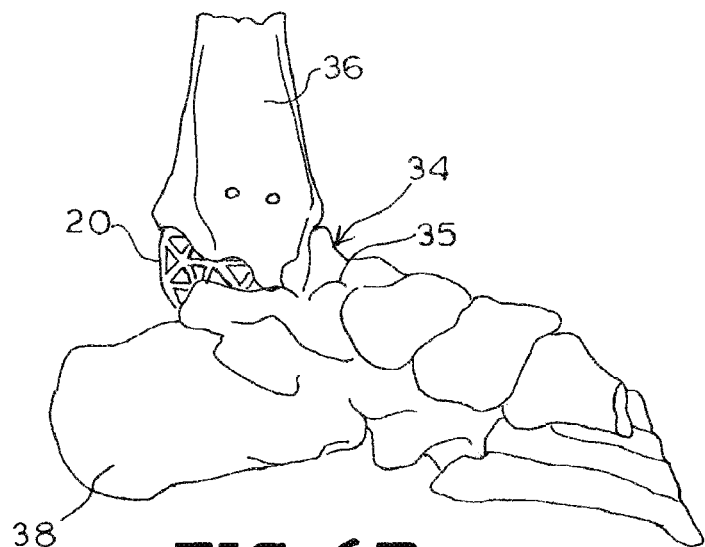
FIG. 6B is an opposite side elevation view of the bone implant positioned in a foot and ankle joint as shown in FIG. 6A.
Figure 6C:
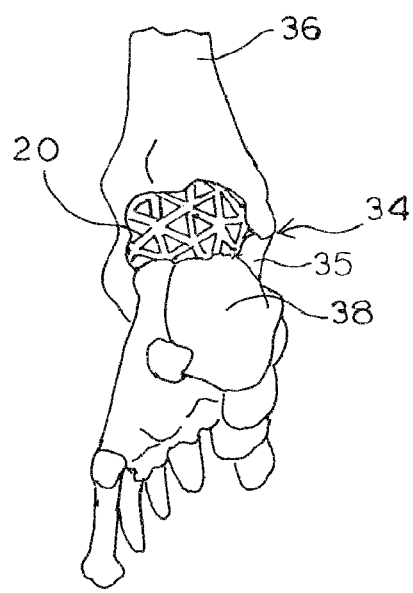
FIG. 6C is a rear perspective view of the bone implant positioned in a foot and ankle joint as shown in FIG. 6A.
Figure 6E:
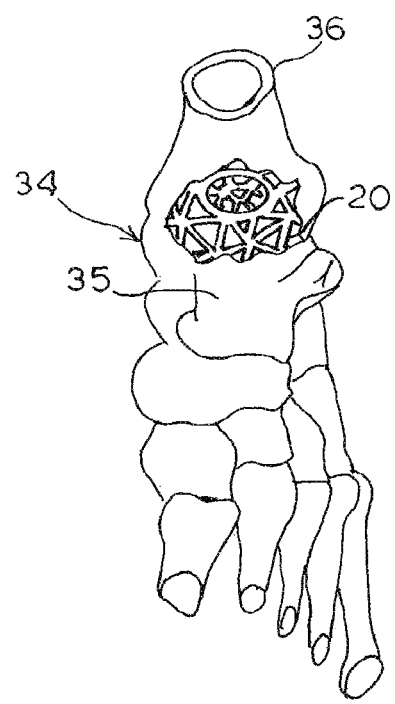
FIG. 6E is a top perspective view of the bone implant positioned in a foot and ankle joint as shown in FIG. 6A.
Figure 6D:
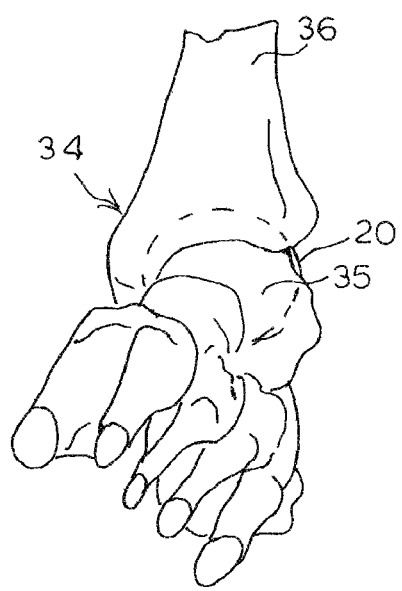
FIG. 6D is a front perspective view of the bone implant shown in phantom positioned in a foot and ankle joint as shown in FIG. 6A.
Figure 7A:
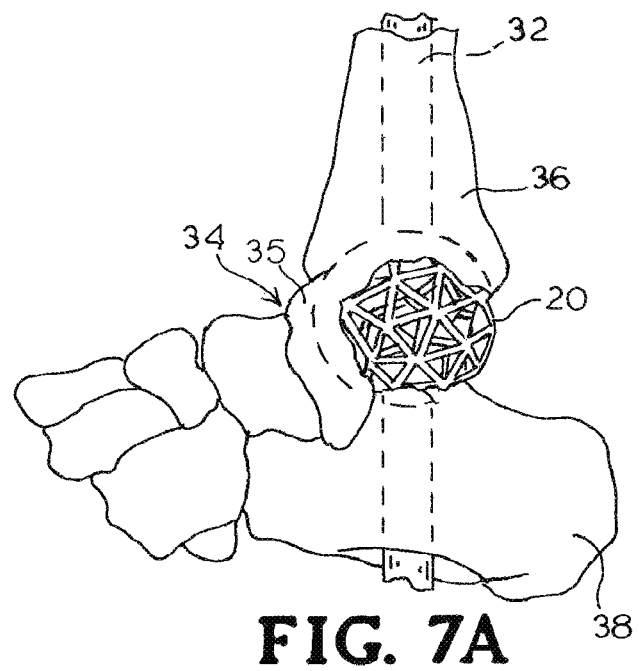
FIG. 7A is a side elevation view of the bone implant as shown in FIG. 1 positioned in a foot and ankle joint and a portion of an intramedullary nail shown in phantom.
Figure 7B:
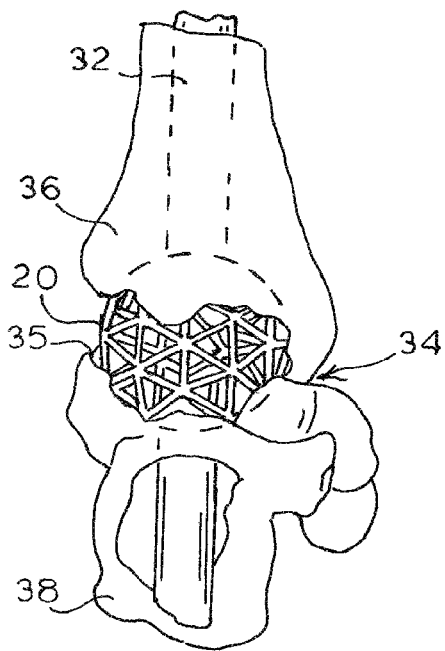
FIG. 7B is a rear perspective view of the bone implant positioned in a foot and ankle joint as shown in FIG. 7A.
Figure 7C:
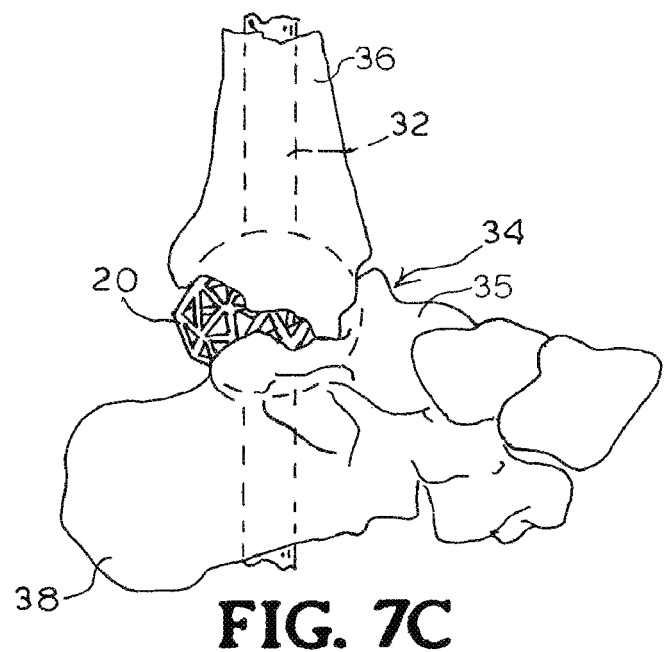
FIG. 7C is an opposite side elevation view of the bone implant positioned in a foot and ankle joint as shown in FIG. 7A.
Figure 7D:
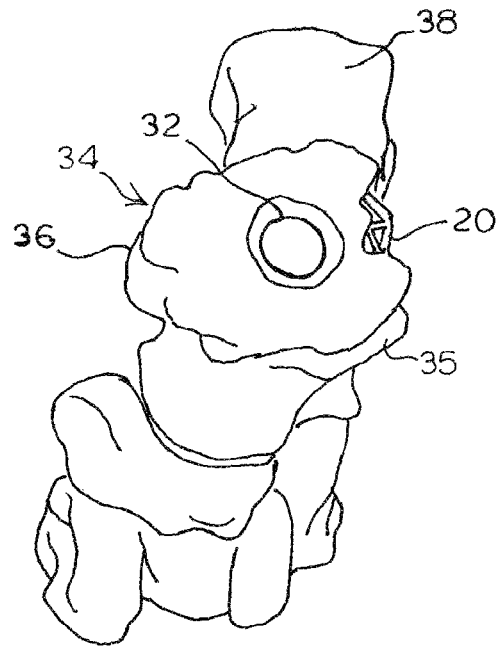
FIG. 7D is a top plan view of the bone implant positioned in a foot and ankle joint as shown in FIG. 7A.
Figure 7E:
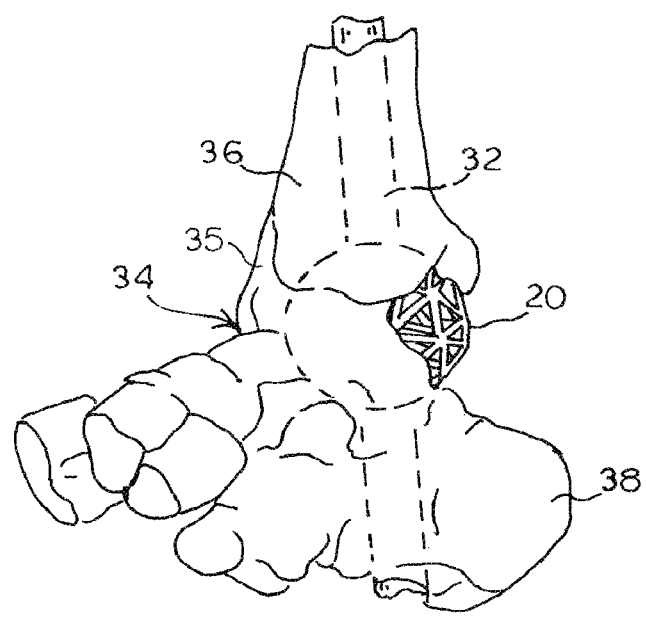
FIG. 7E is an up-close view of the bone implant positioned in a foot and ankle joint as shown in FIG. 7A.

As shown in the FIGS. 1 and 2, the center portion of the spherical web structure 22 defines a cylindrical passage 30. The central passage 30 is configured to receive an intramedullary nail extending therethrough (FIG. 3).

In the embodiment of the implant 44 shown in FIG. 9, the planar or aspherical portion of the implant 44 accommodates a plate 42 or the like to facilitate attaching the combined porous web structure 45 and the plate 42 to bone using screws 48. For example, where an implant is implanted adjacent to a bony structure, one or more structures may be disposed on or extend from a surface (e.g., an interface plate) of the implant that is intended to contact, and at least partially adhere to, the bony structure during use.

A method is provided that includes the steps of providing an opening in a foot or ankle 34 of a human, and installing into the opening the implant 20, 44, 50, 54. The implant location is first prepared, including surgical dissection for forming an opening proximate the foot or ankle 34 to the level of proposed implantation. Next, a bone bed can be prepared from the adjacent bony structure either by using a spherical reaming device or using a saw and osteotomes. The bone bed may be formed in either a joint or within a single bone. Bone graft material may be packed in the bone bed or within the porous web structure 22 of the implant 20. The implant 20 is then inserted into the bone bed. The implant 20 may be incorporated into the end surfaces established between an upper tibia bone 36 and an opposite and lower talus bone 38. The shape of at least a portion of the implant 20 allows the bone or the joint surface on either side of the implant 20 to be placed in a preferred position, for example, to correct a deformity. FIGS. 6A-6E show the implant 20 disposed in respective openings of the foot and ankle bones.

In some embodiments, inserting the implant 20 includes positioning the implant 20 adjacent the boney structure, aligning the web structure 22 with a complementary portion of the boney structure, or advancing a contact surface toward the boney structure such that at least the web structure 22 is in contact or near contact with the boney structure. In some embodiments, the implant 20 may be advanced until the contact surface is in contact or near contact with the boney structure, such that at least portion or substantially all of the web structure 22 is disposed in the boney structure.

Figure 8:
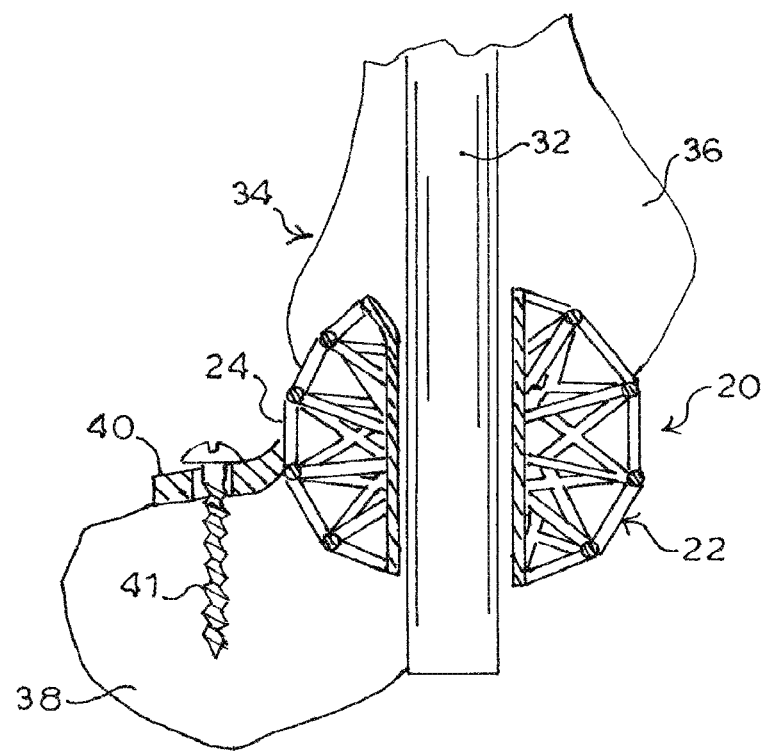
FIG. 8 is a perspective view of another embodiment of a bone implant positioned in a foot and ankle joint and including a fixation device.
Figure 11:
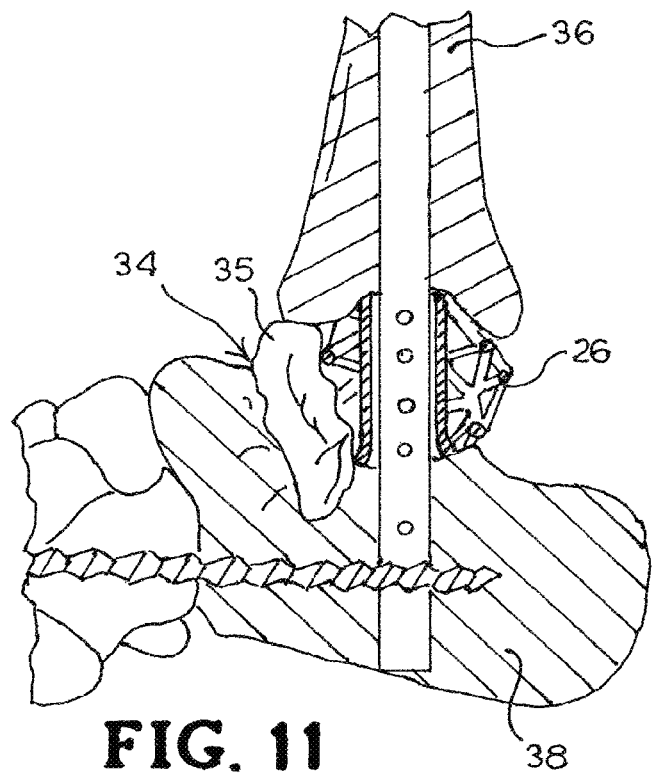
FIG. 11 is a perspective view of fifth embodiment of a bone implant for use in a foot and ankle joint.

The implant 20 then may, or may not be, fixed in place. In one embodiment, an intramedullary nail 32 is inserted into the heel and through the passage 30 in the web structure 22 of the implant 20. The nail 32 is driven into the end of the tibia 36 for fusing the foot and ankle joint 34 (FIGS. 7A-7E). In an embodiment shown in FIG. 8, a tab 40 integral with the web structure 22 may be included on the implant 20. The tab 40 may be secured to adjacent bone with staples, screws, plates, or other means of fixation. FIG. 11 shows openings in the intramedullary nail 32 for receiving at least one screw passing through another part of the foot and ankle joint.

Figure 13:
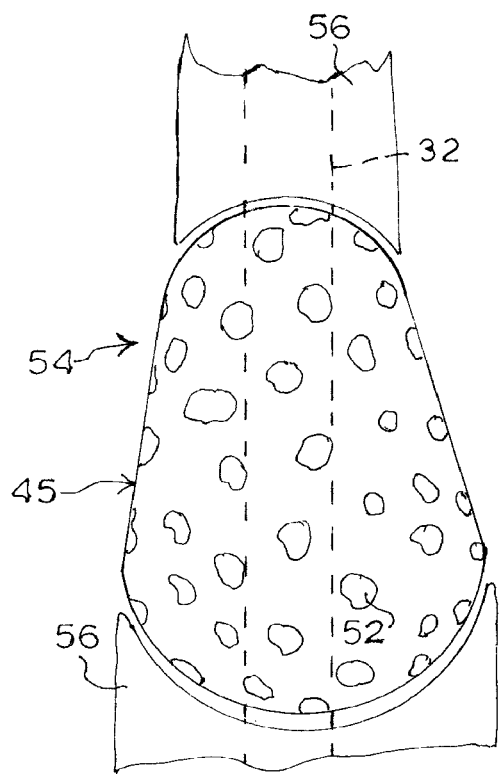
FIG. 13 is schematic elevation view of the third embodiment of the bone implant as shown in FIG. 9 between two portions of bone.

FIGS. 13 and 14 schematically show the implants 44, 54 having an aspherical side and an egg-shape implant contacting adjacent bony structure 56. As depicted, the implants 44, 54 are intended to be disposed between the adjacent bony structures interfacing with bone structure of a foot and ankle joint. The top of the implants 44, 54 may couple to a portion of the first bony structure 56 disposed above the implants and the bottom contact faces 28 may couple to the second bony structure disposed below implants 44, 54.

Once the implant is positioned in the foot and ankle joint 34, the access point to the implant site may be closed using sutures or other closure devices.

Although the bone implant has been shown and described in considerable detail with respect to only a few exemplary embodiments thereof, it should be understood by those skilled in the art that I do not intend to limit the invention to the embodiments since various modifications, omissions and additions may be made to the disclosed embodiments without materially departing from the novel teachings and advantages, particularly in light of the foregoing teachings. Accordingly, I intend to cover all such modifications, omission, additions and equivalents as may be included within the spirit and scope of the bone implant as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An implant for use in the fusion of a plurality of bones, the implant comprising:
   a plurality of struts defining a generally spherical component, the plurality of struts further defining a channel having terminal ends and extending through the component and the terminal ends of the channel, wherein the struts defining the terminal ends of the channel further define respective perimeters of terminal ends of the component.

2. The implant according to claim 1, further comprising a tab integral with and extending from the component, the tab having a hole extending therethrough configured for receiving a fastener for securing the component to a bone surface.

3. The implant according to claim 2, wherein the tab extends at an obtuse angle relative to the channel.

4. The implant according to claim 1, wherein the struts defining the terminal ends of the component further define a plane.

5. The implant according to claim 4, wherein the tab extends within a plane transverse to a channel axis defined by the channel.

6. The implant according to claim 1, wherein the channel has a cylindrical shape and extends along an axis that is offset relative to a center of the component.

7. The implant according to claim 1, further comprising an intramedullary nail configured to extend through the channel.

8. The implant according to claim 7, wherein the intramedullary nail includes a plurality of holes extending therethrough in a direction transverse to a longitudinal axis of the nail.

9. The implant according to claim 8, wherein at least two of the holes extending through the nail are not mutually parallel.

10. The implant according to claim 1, wherein the plurality of struts defines at least three convex shapes forming a first set of outer surfaces of the implant.

11. The implant according to claim 10, wherein the implant is configured for use in the fusion of respective reconditioned surfaces established on a distal end of a tibia, a talus, and a calcaneus of an ankle joint, wherein the at least three convex shapes forming the first set of outer surfaces are adapted to be disposed against so as to interface in a complementary manner with respective reconditioned bone surfaces established on each of a tibia, a talus, and a calcaneous.

12. The implant according to claim 1, wherein the plurality of struts defining the channel form polygonal openings.

13. The implant according to claim 1, wherein the plurality of struts define an internal web structure extending between an outer surface of the component and the channel.

14. The implant according to claim 1, wherein the component defines a planar outer surface intersected by the channel.

15. The implant according to claim 14, further comprising a planar plate member lying on and along the planar outer surface of the component.

16. The implant according to claim 14, wherein the plate member includes a plurality of holes configured for receiving a corresponding plurality of fasteners.

17. The implant according to claim 1, wherein the plurality of struts define a first subcomponent of the component defining polygonal openings, and wherein the component is further defined by a second subcomponent having irregular curved pores.

18. The implant according to claim 17, wherein at least some of the irregular curved pores are defined by an outer surface of the component and at least some of the irregular curved pores are defined by the channel.

19. The implant according to claim 17, wherein the irregular curved pores are randomly located.

20. The implant according to claim 1, wherein the component defines a component central axis, and the channel defines a channel central axis offset from the component central axis.

* * * * *